(12) United States Patent
Bevis et al.

(10) Patent No.: US 7,061,598 B1
(45) Date of Patent: Jun. 13, 2006

(54) DARKFIELD INSPECTION SYSTEM HAVING PHOTODETECTOR ARRAY

(75) Inventors: Christopher F. Bevis, Los Gatos, CA (US); David W. Shortt, Milpitas, CA (US)

(73) Assignee: KLA-Tencor Technologies Corporation, San Jose, CA (US)

( * ) Notice: Subject to any disclaimer, the term of this patent is extended or adjusted under 35 U.S.C. 154(b) by 281 days.

(21) Appl. No.: 10/315,340

(22) Filed: Dec. 9, 2002

Related U.S. Application Data

(60) Provisional application No. 60/414,206, filed on Sep. 27, 2002.

(51) Int. Cl.
*G01N 21/00* (2006.01)

(52) U.S. Cl. .............................. 356/237.1; 356/237.4; 356/237.5

(58) Field of Classification Search .. 356/237.1–237.5, 356/241.1–241.6, 238.1, 238.3; 250/559.4–559.45; 382/141, 145, 144, 147, 148, 149; 348/125, 348/126, 128
See application file for complete search history.

(56) References Cited

U.S. PATENT DOCUMENTS

| | | | | | |
|---|---|---|---|---|---|
| 4,173,415 | A | * | 11/1979 | Wyatt | 356/336 |
| 4,511,803 | A | * | 4/1985 | Ross et al. | 250/559.48 |
| 4,583,861 | A | * | 4/1986 | Yamaji et al. | 356/446 |
| 4,710,642 | A | * | 12/1987 | McNeil | 250/559.04 |
| 4,991,971 | A | * | 2/1991 | Geary et al. | 356/446 |
| 5,790,251 | A | * | 8/1998 | Hagiwara | 356/491 |
| 5,798,831 | A | * | 8/1998 | Hagiwara | 356/237.2 |
| 6,034,776 | A | * | 3/2000 | Germer et al. | 356/369 |
| 6,259,521 | B1 | * | 7/2001 | Miller et al. | 356/237.5 |
| 6,271,916 | B1 | * | 8/2001 | Marxer et al. | 356/237.3 |
| 6,534,222 | B1 | * | 3/2003 | Suzuki | 430/5 |
| 6,562,248 | B1 | * | 5/2003 | Subramanian et al. | 216/12 |
| 6,603,541 | B1 | * | 8/2003 | Lange | 356/237.2 |
| 6,661,912 | B1 | * | 12/2003 | Taguchi et al. | 382/145 |
| 2003/0218741 | A1 | * | 11/2003 | Guetta | 356/237.1 |
| 2004/0016896 | A1 | * | 1/2004 | Almogy et al. | 250/559.45 |

FOREIGN PATENT DOCUMENTS

JP          2001281097 A    * 10/2001

OTHER PUBLICATIONS

U.S. Appl. No. 10/315,713, filed Dec. 9, 2002, Entitled: "Surface Inspection System and Method for Using Photo Detector Array to Detect Defects in Inspection Surface", Inventors: Mapoles et al.
Handbook of Optics, vol. 1, Fundamentals, Techniques, and Design, Second Edition, 1995, McGraw-Hill, Inc., pp. 30.4-30.8.

* cited by examiner

*Primary Examiner*—Gregory J. Toatley, Jr.
*Assistant Examiner*—Gordon J. Stock, Jr.
(74) *Attorney, Agent, or Firm*—Beyer Weaver & Thomas LLP

(57) ABSTRACT

A darkfield surface inspection tool of the invention includes an illumination source for illuminating a workpiece and generating a light scattering pattern. The light scattering pattern being configured such that the positions of the light beams of the scattering pattern are uniquely related to the scattering angles of the light beams as they are scattered from the workpiece. The tool also includes a photodetector array positioned at a detector surface to detect the light scattering pattern as it reaches the detector surface. The photodetector array produces an electrical signal that is received by signal processing electronics of the tool and can be used to characterize defects on the workpiece. The invention also includes darkfield surface inspection methods.

9 Claims, 14 Drawing Sheets

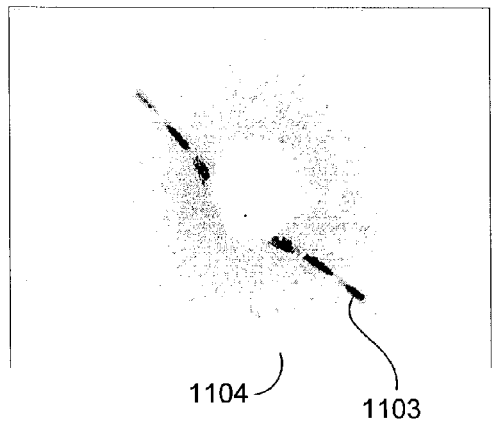
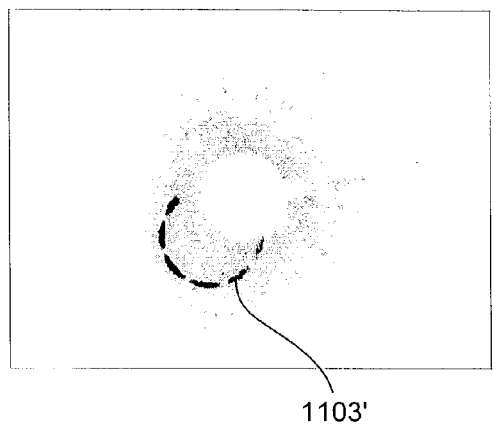
Fig. 11(c)  Fig. 11(d)
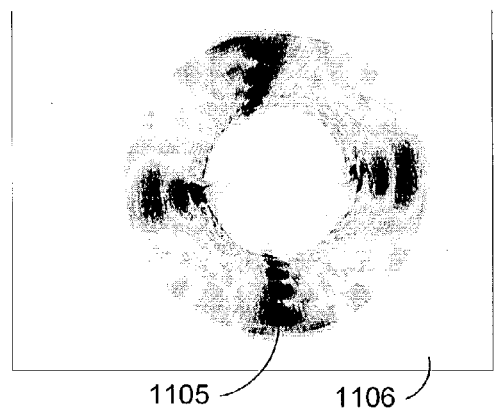
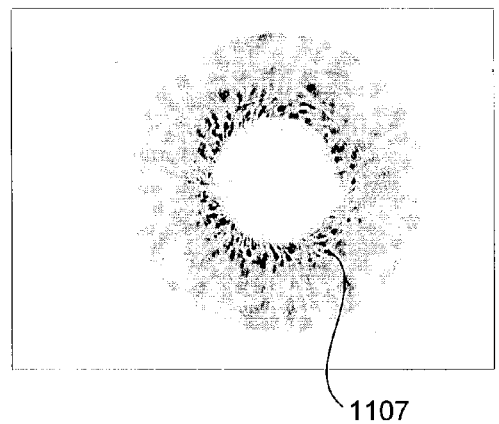
Fig. 11(e)  Fig. 11(f)
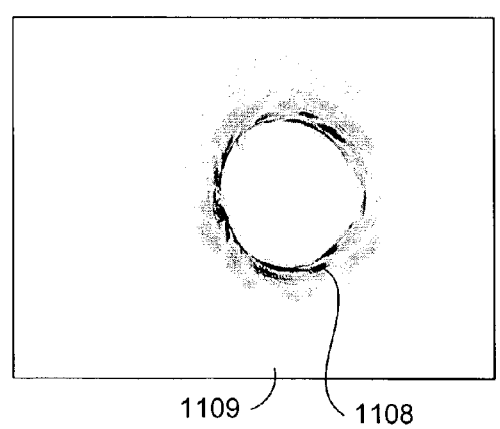
Fig. 11(g)

DARKFIELD INSPECTION SYSTEM HAVING PHOTODETECTOR ARRAY

RELATED APPLICATIONS

This application is claims priority to U.S. Provisional Patent Application Ser. No. 60/414,206, entitled "Darkfield Inspection System Having Photodetector Array", by inventors Christopher F. Bevis et al., filed on Sep. 27, 2002, which is hereby incorporated by reference.

This application is related to the concurrently filed U.S. patent application entitled "Surface Inspection System and Method for Using Photo Detector Array to Detect Defects in Inspection Surface", by inventors Evan R. Mapoles et al., Ser. No. 10/315,713 which is hereby incorporated by reference.

TECHNICAL FIELD

The invention described herein relates generally to surface inspection and testing. In particular, the invention relates to devices and methods for darkfield inspection of semiconductor wafer surfaces or reticle surfaces.

BACKGROUND

For many years, darkfield scanning methodologies have been used to scan surfaces. Darkfield scanning makes use of light scattered or diffracted by the surface to characterize and examine features of the surface. As used herein, scattered light shall refer to both scattered light and diffracted light. FIG. 1 is a cross-section view of an illuminated surface used to illustrate aspects of darkfield scanning. An illumination source 101 projects a light beam I (also referred to herein as the incident beam) onto the surface 102 being examined. A portion of the incident beam I is reflected by the surface as the reflected beam R. If the surface 102 was perfectly reflective, the entire incident beam I would be reflected. However, most surfaces have a variety of characteristics which cause a portion of the light from an incident beam I to be scattered. Darkfield scanning makes use of this scattered light.

One particular surface feature that causes light scattering is referred to as a defect. The detection, quantification, and classification of defects is important in many areas. In particular, defect detection and analysis are important in semiconductor processing. Defects include, but are not limited to, pits, bumps, scratches, and a number of other features, which mar the surface 102. Thus, the light of an incident beam I is often subject to some degree of scattering. FIG. 1 illustrates a typical incident beam I having a light scattering pattern schematically depicted by a plurality of scattered light rays 103, 104, 105, and 106, which are scattered by a surface defect 108. The depicted plurality of rays can represent a continuous angular distribution of light scattered and diffracted by the surface.

Known darkfield inspection tools use a single discrete photodetector element (for example a PMT) to detect the light scattered from the inspection surface. Some designs use as many as three or four distinct and widely separated discrete photodetector elements. Such discrete photodetector element(s) are positioned so that they are not in the path of the reflected beam R. This results in a detection field where the background (the field) is dark. The scattered light received by the detector provides a representation of the surface 102 whereby the surface defects show up as lighter regions against the dark background or field. Hence, the name darkfield scanning.

FIG. 2 depicts another cross-section view of a surface being scanned using darkfield scanning. The surface 102 is illuminated by an incident beam I, a portion of which is reflected as reflected beam R. Another portion of the light of the incident beam I is scattered. Here, the scattered light is schematically depicted by the rays $S_1$, $S_2$, and $S_3$. Each of the scattered light rays $S_1$, $S_2$, and $S_3$ have scattering angles associated therewith. Because FIG. 2 is a two dimensional representation of a three dimensional reality, only one scattering angle is depicted for each scattered light rays $S_1$, $S_2$, and $S_3$. In the depiction of FIG. 2, the scattering angles are measured from the illuminated surface 102. Thus, scattered light ray $S_1$ is associated with scattering angle $A_1$. Scattered light ray $S_2$ is associated with scattering angle $A_2$. Scattered light ray $S_3$ is associated with scattering angle $A_3$, and so on. The scattering angles $S_1$, $S_2$, $S_3$ depicted here are determined from the surface 102. However, scattering angles can be determined in a variety of different and also in a variety of coordinate systems. For example, the scattering angles can be determined from a line normal to the surface 102.

FIG. 3 is a schematic three-dimensional view of an incident light beam I and a scattered light ray 301. The depicted coordinate system is an (x, y, z) coordinate system with a surface lying in the x-z plane. One scattering angle is depicted as $\phi$, which is the angle from the x-z plane. The other depicted angle is $\theta$, which is the angle from the y-z plane. As was previously stated, many other ways of referring to scattered light ray angles are known and can be used.

One type of conventional darkfield surface inspection device 400 is depicted in FIG. 4. An ellipsoidal mirror 420 is positioned over an inspection surface 402. An incident light beam 401 is directed onto an inspection surface 402. Schematically depicted are a reflected light beam 403 and many scattered light beams 410, 411, 412, 413, 414, 415, and 416. The device includes a first discrete photodetector 421 and a second discrete photodetector 422 positioned above the ellipsoidal mirror 420. A portion of the scattered light (depicted here by scattered light beams 410, 411, 412, 413, 414, 415, and 416) passes through an opening O in the ellipsoidal mirror 420. The center portion of the scattered light beams (schematically depicted by beams 415, 416) passes through a lens 423 which directs the light onto a central mirror 424 which reflects the central beams 415, 416 so they converge at a side focal point 425. The second discrete photodetector 422 is positioned at the side focal point 425 to receive the central beams 415, 416. At the same time, an outer portion of the scattered light beams (schematically depicted by beams 410, 411, 412, 413, 414) passes through the opening in the ellipsoidal mirror 420 and is reflected by the ellipsoidal mirror 420 onto a top focal point 426. The ellipsoidal mirror 420 is specifically designed to concentrate the outer portion of the scattered light beams 410, 411, 412, 413, 414 onto the top focal point 426. Also, the first discrete photodetector 421 is specifically positioned at the top focal point 426. Frequently, the discrete photodetectors 421, 422 include optical feed fibers that convey the focused light to a single discrete photodetector which is commonly a single photodiode or a single photo-multiplier tube (PMT). By integrating light information from the first discrete photodetector 421 and the second discrete photodetector 422 the presence of a defect can be determined.

FIGS. 5(a) and 5(b) are depictions of a portion of a darkfield surface inspection device of the type described in FIG. 4. In FIG. 5(a), a first discrete photodetector 501 is positioned above a focal point 502 (corresponding to another focal point 426 of FIG. 4). Thus, the scattered light is now diverging 503 and out of focus. Large amounts of signal are lost to first discrete photodetector 501 making this a disadvantageous configuration. In FIG. 5(*b*), a first discrete photodetector 501 is positioned below focal point 502 (also corresponding to another focal point 426 of FIG. 4). Thus, the scattered light 504 is still out of focus and still converging when it reaches the detector 501. Again, large amounts of signal are lost to the first discrete photodetector 501 making this a disadvantageous configuration. This model also applies to the second discrete photodetector (depicted as 422 of FIG. 4). Thus, the prior art systems employ one or more discrete photodetectors to detect scattered light. A disadvantage of such a configuration is that the discrete photodetectors of these implementations are optimized for making measurements of light intensity. Such a configuration can, at best, only collect light over a finite range of angles and is not able to capture any significant amount of spatial information concerning the scattered light An additional problem with discrete photodetector systems is that, when they are applied to patterned surfaces (e.g., the patterned surfaces of semiconductor wafers), light scattered from the patterned surface is diffracted by the patterned surface in a diffraction pattern. Such a diffraction pattern produces a pattern of light spots a certain discrete angles that are associated with the surface pattern. In an effort to address this problem, conventional approaches use selective filtering to filter out the light spots. In some implementations this is known as "fourier filtering". An artifact of such fourier filtering is that certain scattering patterns produced by defects will be masked making certain defects difficult to detect. Moreover, as surface patterns become more complicated, as is the case in modern VLSI circuit structures, the scattering patterns become so complicated that it becomes difficult to filter the scattering pattern at all. So, for the most part, it is very difficult to correctly assess whether a scattering pattern is due to defects of normal surface structure. Thus, additional methods and tools must be used to inspect the surface for the presence of defects. This problem slows the inspection process considerably. The cumulative effect of these shortcomings is that more machines and people are required to conduct surface inspection thereby increasing the cost of such inspections.

Thus, conventional inspection systems are very sensitive to photodetector misalignment and variations in individual photdetector characteristics. This problem becomes worse when many individual discrete photodetector elements are employed. As such, alignment difficulties and other related issues put an upper limit on the number of discrete photodetector elements that can be reasonably employed in a given inspection device. Additionally, such conventional devices require the the implementation of filtering for patterned surfaces, are subject to giving false positive readings, and, although they can detect the presence of many defects, they can not determine the type of defects.

For these and other reasons, improved darkfield inspection tools and methodologies are needed.

SUMMARY OF THE INVENTION

In accordance with the principles of the present invention, darkfield inspection tools and methodologies are disclosed.

In one embodiment, an inspection tool includes an illumination source for directing a light beam onto a workpiece to generating a light scattering pattern such that the position of scattered light beams are uniquely related to scattering angles as the light from the scattering pattern reaches an optical detector surface. A photosensitive detector array positioned at the optical detector surface detects the scattered light and converts it to an electrical signal that is used by processing circuitry to characterize defects in the workpiece.

A toot embodiment includes an illumination source for illuminating a workpiece. The tool also includes a light-shaping element that receives light scattered from the illuminated surface of the workpiece and shapes that light into a resultant light distribution. As the light distribution reaches an optical detector surface, the light distribution is uniquely related to the scattering angles of the light scattered from the surface. The tool includes a photosensitive detector array positioned at the optical detector surface such that it receives at least a portion of the resultant light distribution.

Another embodiment of the darkfield surface inspection tool uses a light-shaping element arranged to shape the light scattered from the surface into an unfocused light distribution such that the light distribution is uniquely related to scattering angles of the light scattered from the surface. A photosensitive detector array is positioned to receive at least a portion of the unfocused light distribution.

The invention also includes a darkfield surface inspection method comprising illuminating an inspection surface with a light beam, shaping light scattered from the inspection surface into a light distribution such that the position of the light distribution as it passes through an optical detector surface is uniquely related to scattering angles of the light scattered from the inspection surface, and detecting the light distribution at the optical detector surface.

These and other aspects of the present invention are described in greater detail in the detailed description of the drawings set forth hereinbelow.

BRIEF DESCRIPTION OF THE DRAWINGS

The following detailed description will be more readily understood in conjunction with the accompanying drawings, in which:

FIG. 1 is a cross-sectional view showing an incident light beam being scattered from a semiconductor wafer surface.

FIG. 2 is a cross-sectional view showing an incident light beam being scattered from a semiconductor wafer surface and showing scattering angles for scattered light beams.

FIG. 3 is three-dimensional perspective view of scattering angles for a light beam being scattered from a surface.

FIG. 6(*b*) is a perspective view of a lens element uniquely mapping the scattering angles of the scattered light beams to a position of on a photodetector array in accordance with the principles of the present invention.

FIGS. 6(*c*) and 6(*d*) are cross-sectional views of a lens element and suitable detection planes that can uniquely map the scattering angles of the scattered light beams to a suitable positioned photodetector array in accordance with the principles of the present invention.

FIGS. 11(a)–11(g) are image diagrams depicting some example images that can be used to distinguish defects from one another in accordance with the principles of the present invention.

It is to be understood that, in the drawings, like reference numerals designate like structural elements. Also, it is understood that the depictions in the Figures are not necessarily to scale.

DETAILED DESCRIPTION OF THE DRAWINGS

The present invention has been particularly shown and described with respect to certain embodiments and specific features thereof. The embodiments set forth herein below are to be taken as illustrative rather than limiting. It should be readily apparent to those of ordinary skill in the art that various changes and modifications in form and detail may be made without departing from the spirit and scope of the invention.

The following detailed description describes various embodiments of darkfield inspection tools and methods for their use. In particular, embodiments of the present invention illuminate a portion of an inspection surface to create scattered light. The scattered light from the surface is received by one or more photo-detector arrays that enable the inspection tool to detect and characterize defects in the inspection surface. In some embodiments, scattered light from the surface is received light-shaping element and shaped to create suitable light output beams, which are then detected by photodetector arrays. These output beams are configured such that the position of the output beams are uniquely related to scattering angles of the scattered light beams. As a result, each light scattering pattern can be characterized by the angular distribution of the light intensity in the scattering pattern.

Figure 1:
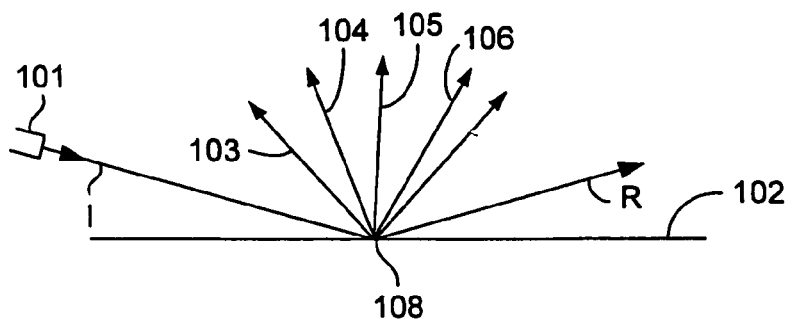
FIGS. 1–3 illustrate aspects of light scattering used in darkfield inspection tools.
Figure 2:
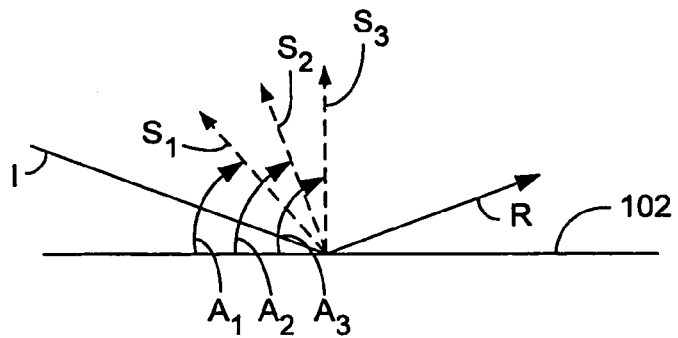
Figure 3:
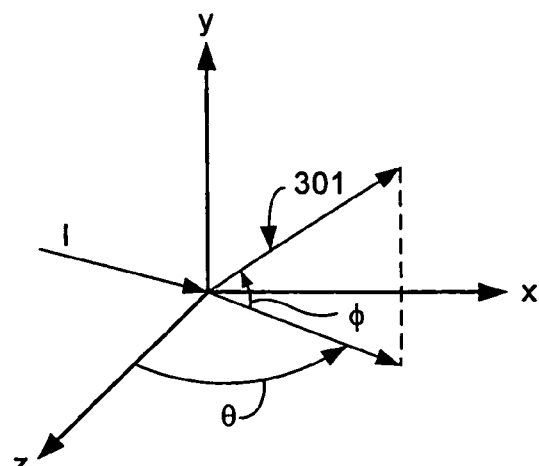
Figure 4:
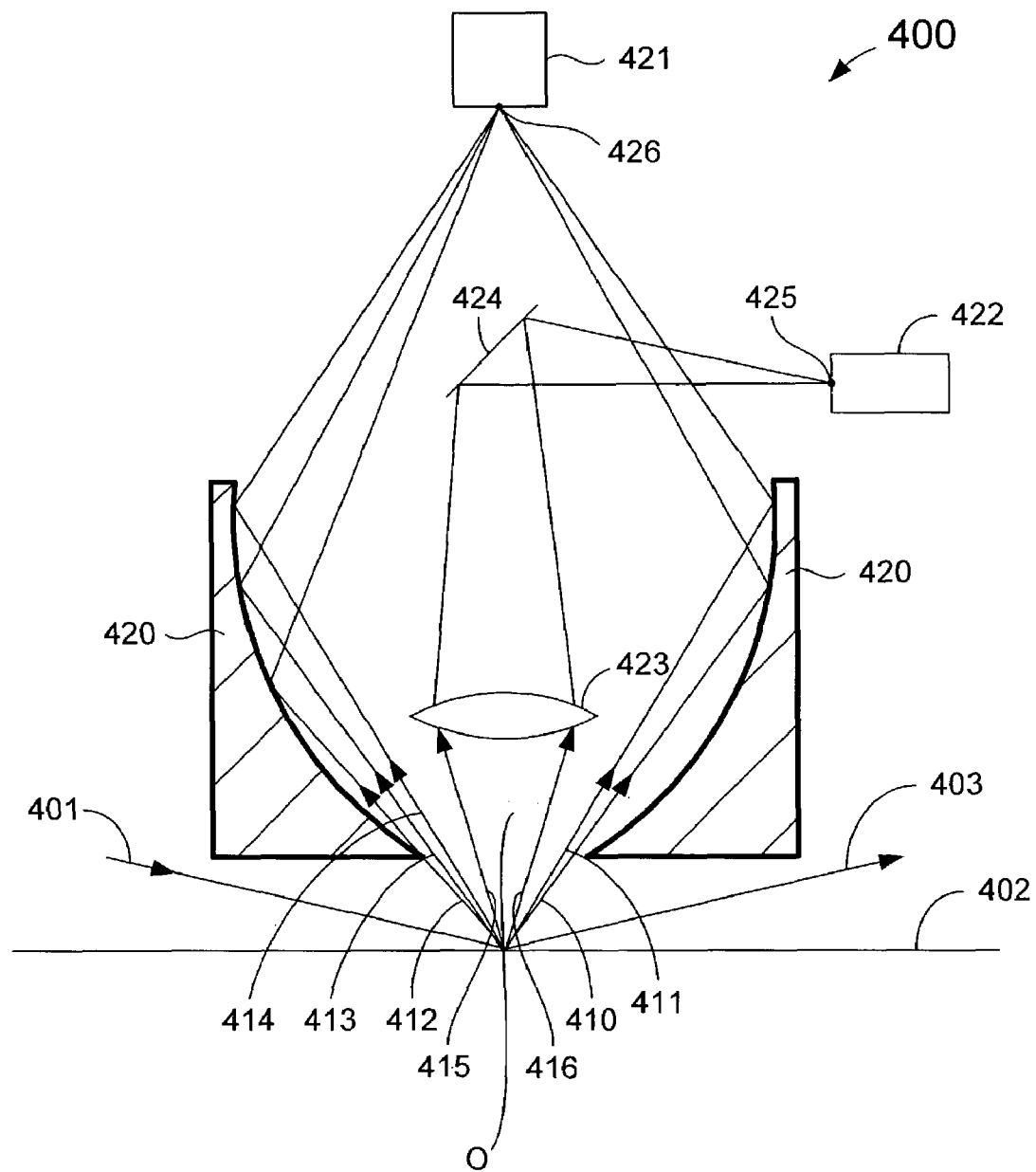
FIG. 4 is a cross-sectional view of a conventional darkfield scanning apparatus.
Figure 5A:
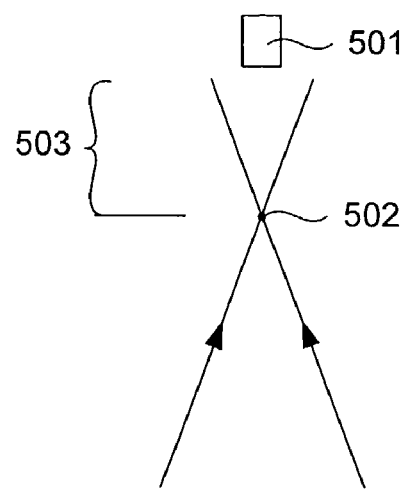
FIGS. 5(*a*) and 5(*b*) are cross-sectional views of a portion of a known darkfield scanning apparatus showing a conventional discrete photodetector positioned both above and below a focal point.
Figure 5B:
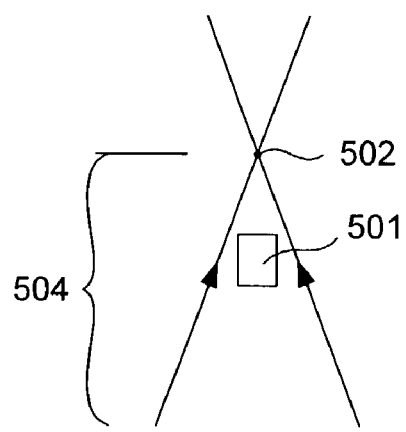
Figure 6A:
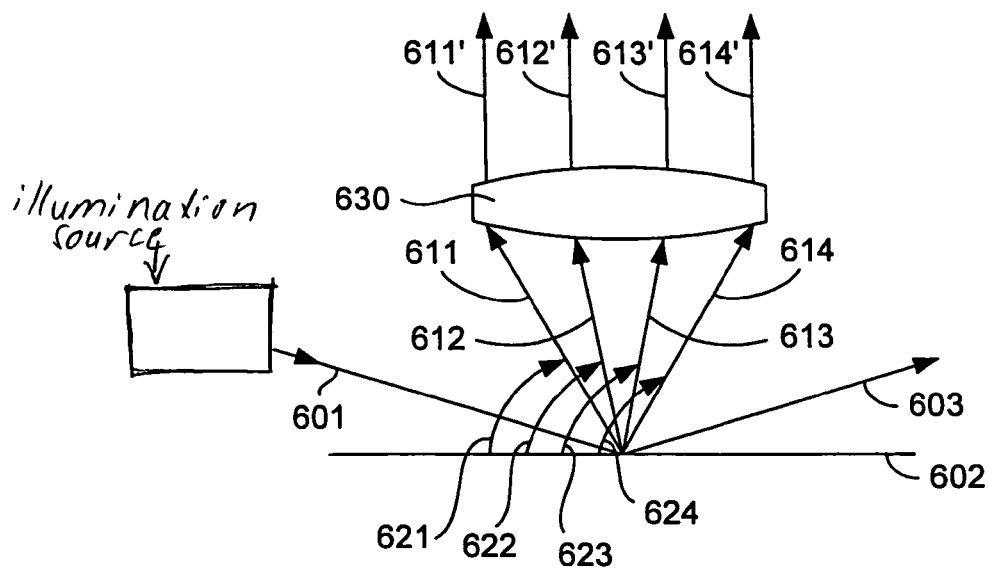
FIG. 6(*a*) is a cross-sectional view of a lens element that can uniquely map the scattering angles of the scattered light beams to a position of an output beam in accordance with the principles of the present invention.
FIGS. 6(e)–6(k) are plan views of example photosensor embodiments in accordance with the principles of the present invention.

One aspect of the invention is depicted in FIG. 6(a). An incident beam 601 illuminates a surface to be inspected 602. Although the apparatus and techniques disclosed herein can be used to inspect any type of surface, the invention finds particular applicability to semiconductor wafer surfaces. This invention finds special utility when applied to patterned semiconductor wafer surfaces, such as those surfaces having semiconductor and/or metallization structures, and the like, formed thereon. As previously discussed, a portion of the incident light beam 601 is reflected as reflected beam 603. Another portion of the incident light beam 601 is scattered by the surface 602. This scattered light is schematically depicted as scattered light beams 611, 612, 613, and 614. Each of scattered light beams has associated therewith at least one corresponding scattering angle (depicted here as scattering angles 621, 622, 623, and 624). Because FIG. 6 is a two-dimensional representation of a three-dimensional reality only one of the at least one scattering angle is depicted. Although, as explained previously with respect to FIGS. 2 and 3, each scattered light beam 611, 612, 613, and 614 can have a scattering angle extending into or out of the page. Also, each inspection point on the surface generates a light scattering pattern that is associated with the surface topography of the inspection point.

With continued reference to FIG. 6(a), a portion of the scattered light is received by a light shaping element that is configured to shape the incoming scattered light beams into an output distribution such that the position of the light from the output light beams uniquely related to the scattering angles of the incoming scattered light beams. This is feature is depicted in FIG. 6(a) where the beam shaping element comprises lens element 630. The lens element 630 is configured such that the incoming scattered light beams 611, 612, 613, and 614 are shaped into an output light distribution such that the position of the light from output light beams 611', 612', 613', and 614' is uniquely related to scattering angles 621, 622, 623, and 624 of the scattered light beams 611, 612, 613, and 614. In this way, photodetector arrays can be used to determine the angular distribution of the light intensity of a light scattering pattern.

In the depicted embodiment, the lens element 630 is a collimator. The collimator shapes the received scattered light beams 611, 612, 613, and 614 into a plurality of parallel output light beams 611', 612', 613', and 614'. These output beams have an output light distribution configured such that the position of each output light beam, as it passes through a detection surface is uniquely related to the scattering angles of the incoming scattered light beams. By detecting the angular distribution of the light intensity of a light scattering pattern (e.g., the intensity of output light beams 611', 612', 613', and 614) the associated inspection point can be characterized.

Figure 6B:
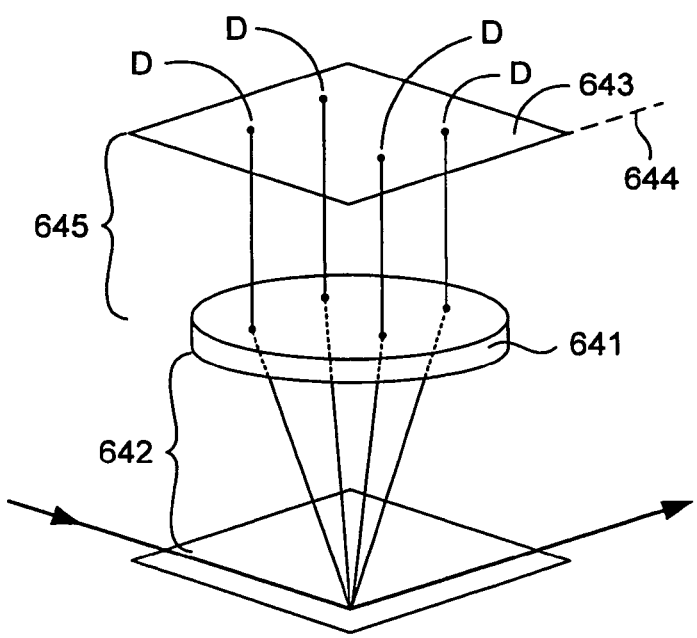

FIG. 6(b) depicts an angular distribution of the light intensity of a light scattering pattern as it is projected onto a photodetector array 643 positioned at a detection plane 644. The relationship between the scattering angles of light rays (beams) scattered from the surface and their two-dimensional position on a photodetector array surface as they are received by the photodetector array is shown by way of example. Scattered light beams are said to be uniquely related to their associated output beams when each scattered light beam having different scattering angles maps to a different location on the detection surface. This means that the specific location where the incoming scattered light beams impinge on the detection surface is dependant on the scattering angles of the scattered light beams. One such a light distribution is illustrated in FIG. 6(b). In the depicted embodiment, the scattered light beams 642 are collimated as they pass through the lens element 641 forming a plurality of parallel output beams 645. The collimated output beams 645 are detected by the photodetector array 643 positioned at a detection plane 644. As shown, each of the scattered beams 642 is output to a separate two-dimensional position D on the detector 643 depending on the scattering angles. It is pointed out that it is not required that the scattered light beams 642 be collimated by the lens element 641. The output beams 645 can be diverging, or in some embodiments, even converging. All that is necessary is that there be a unique one-to-one relationship between beam angle of the scattered light beams and beam position of an associated output beam.

Rather than use a single, or even several, discrete photodetectors, the present invention uses a photodetector array 643. One common implementation is a two-dimensional photodetector array 643 such as a CCD (charge coupled device) detector array. Many, other types of devices can also be used including, but not limited to, CMOS arrays, multicathode PMT's, photodiode arrays, and other array photodetectors known to persons having ordinary skill in the art. These photodetector arrays can be shaped and arranged into a variety of different configurations. FIGS. 6(e)–6(k) show a number of plan views of possible photodetector array configurations. This list is merely intended as a generalized depiction of some possible array configurations and is not intended to be limiting. FIG. 6(e) depicts a planar rectangular photodetector array. FIG. 6(f) depicts a planar hexagonal photodetector array comprising, for example, a plurality of hexagonal photodetector elements. FIG. 6(g) depicts a planar cruciform photodetector array. FIG. 6(h) depicts a planar "linear" photodetector array. FIG. 6(i) depicts a planar circular photodetector array with the photodetector elements having a number of different shapes. FIG. 6(j) depicts a plurality planar rectangular photodetector arrays arranged in a desired configuration. FIG. 6(k) depicts a plurality planar linear photodetector arrays arranged in a desired configuration. Many other configurations can be used. Also, in addition to planar photodetector arrays, the photodetector arrays can be formed into many different curved surfaces whose properties and characteristics are known to persons having ordinary skill in the art.

Figure 6C:
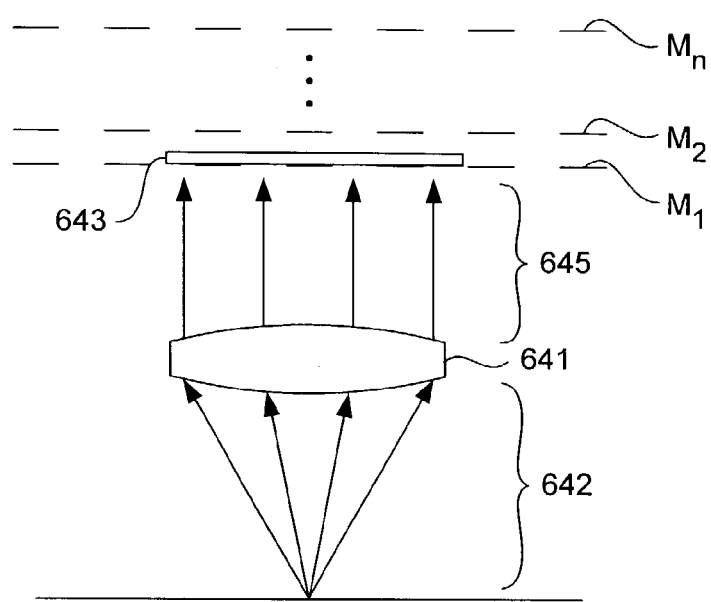
Figure 6D:
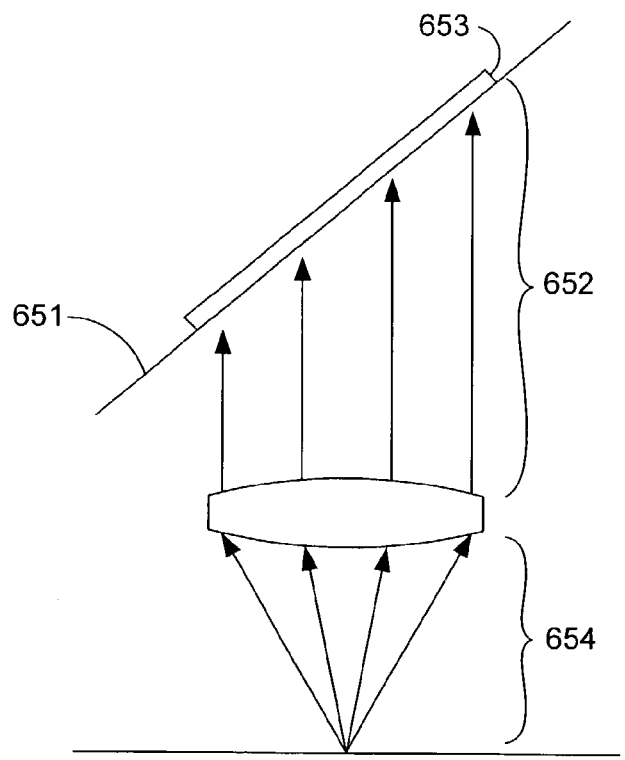
Figure 6I:
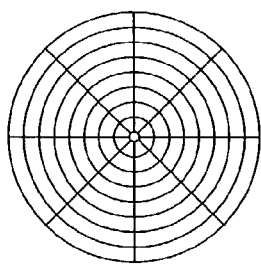
Figure 6H:
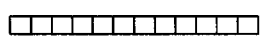
Figure 6K:
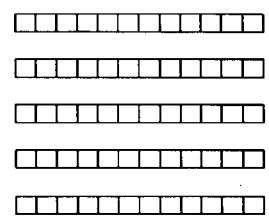
Figure 6G:
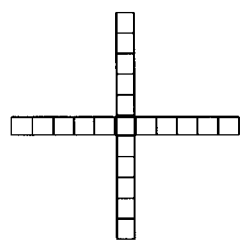
Figure 6F:
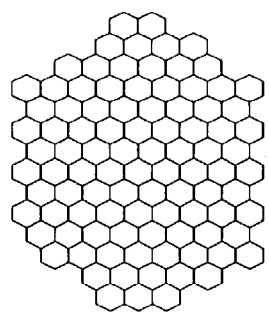
Figure 6J:
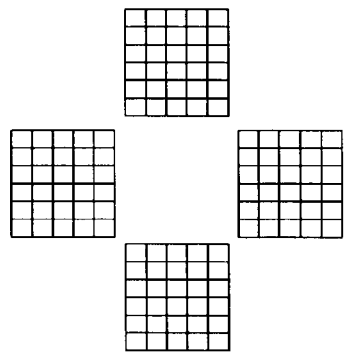
Figure 6E:
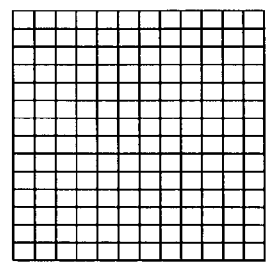

As shown in FIG. 6(c), a lens element 641 has collimated the scattered light beams 642. The collimated output beams 645 can be detected at many different detection planes $M_1$, $M_2$, ... $M_n$ while still uniquely mapping the position of the output beams 645 to the scattering angles of the scattered light beams 642. In this embodiment, the detection planes $M_1$, $M_2$, ... $M_n$ are said to be fourier planes. Fourier planes are well known to those having ordinary skill in the art. Such Fourier planes are well understood and discussed in numerous optics references. For example, the "Handbook of Optics, Volume 1, Fundamentals, Techniques, and Design (2$^{nd}$ Ed.)" (1995) (Edited by Bass, M., Van Stryland E. W., Williams, D., and Wolfe, W.), which is incorporated by reference, discusses Fourier planes (e.g., at pp. 30.5–30.8). Although fourier planes are useful detection planes, other planes can be used. In fact, in addition to flat planes, other surfaces and orientations can be used. For example, in the depicted embodiment the detection plane $M_1$ is oriented such that the collimated output light beams 645 are all incident on the photodetector array 643 at an angle that is are orthogonal to the photodetector array 643 (and the detection plane $M_1$). In an alternative configuration, the inventors contemplate that the detection plane can be at a non-orthogonal angle to the incident output beams. This is illustrated in FIG. 6(d) where a photodetector array 653 is positioned in a detection plane 651 that lies transverse to the output beams 652 but not orthogonal to the direction of propagation of the output beams 652. In such an arrangement there is still a unique relationship between the scattering angles of the scattered light beams 654 and the positions of the output beams 652 as they irradiate the photodetector array 653.

It is important to note that the inventors contemplate light shaping elements where the lens element is not a collimator. Instead, such lens elements can be used to create diverging or converging output beams. All that is necessary is that the lens element shape the output beams such that the position of each light ray of the output beam be uniquely associated with the scattering angles of that ray as it is scattered from the inspection surface.

Figure 7:
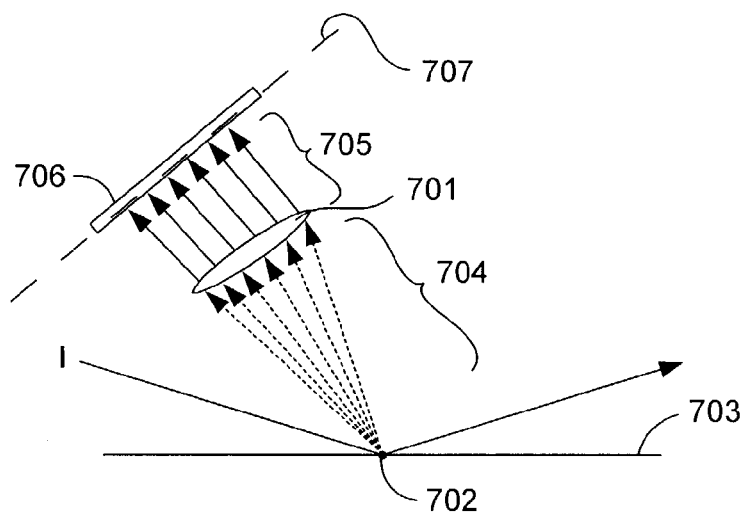
FIG. 7 is a cross-sectional view of one embodiment implementing a lens element in a darkfield inspection tool in accordance with the principles of the present invention.

FIG. 7 depicts another embodiment of a darkfield inspection tool. The lens element 701 is not positioned immediately above the point 702 (the inspection point) where the incident light beam I strikes the surface 703 of the object being inspected ("workpiece"). Rather, the lens element 701 is positioned at an offset angle with respect to the workpiece 703. As before, the scattered light 704 is shaped by the lens element 701 (here, a collimator) to produce parallel output beams 705 that irradiate a photodetector array 706 positioned at a monitor plane 707. As explained with respect to the embodiments above, in this embodiment the scattered light beams 704 each uniquely map to a unique two-dimensional position on the photodetector array 706 positioned in the detection plane 707. And again, the two-dimensional position is uniquely related to the scattering angles of the scattered light beams 704.

Figure 8:
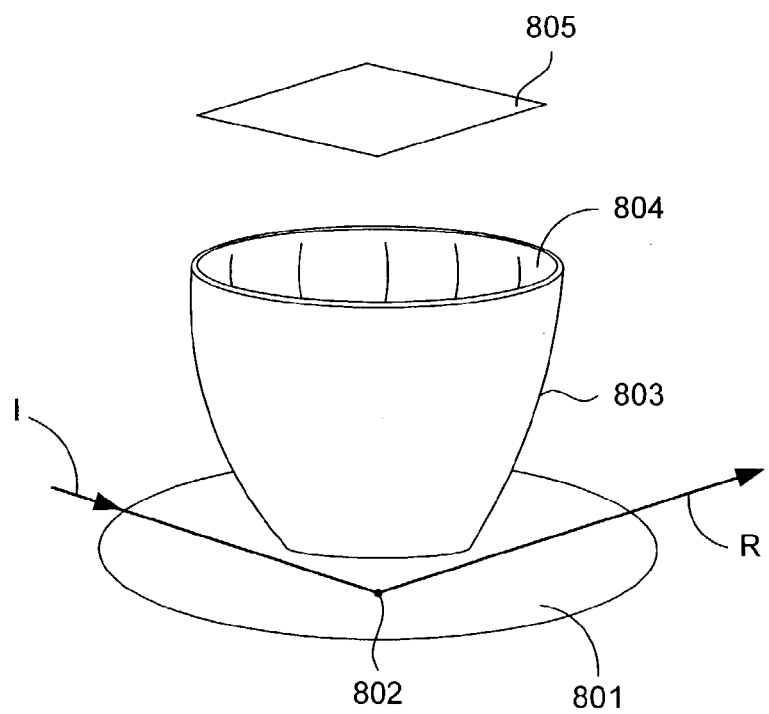
FIG. 8 is a perspective view of one embodiment implementing a reflector element in a darkfield inspection tool in accordance with the principles of the present invention.

In another embodiment of the invention, the light-shaping element of the darkfield inspection tool is replaced with a reflector element. FIG. 8 is a schematic perspective view of such an embodiment. Again, the embodiment of FIG. 8 depicts a reflective element for shaping scattered light into a light distribution whereby the scattered light uniquely maps to a specific two-dimensional position on a photodetector array. With reference to FIG. 8, a workpiece 801, in this case a semiconductor wafer, is illuminated with an incident light beam I that impinges on the surface of the work piece 801 at point 802. A portion of the light from the incident beam I is reflected as beam R and a portion of the beam I is scattered (not shown). Some of this scattered light enters the reflector 803 through an opening (not shown) in the bottom of the reflector 803. A reflective surface on the inside 804 of the reflector 803 directs the scattered light upward onto photodetector array 805 positioned at a detection plane. An important aspect of this embodiment is that the photodetector array 805 not be positioned at a focal point of the reflector. In this way, unfocussed light scattered from the surface of the workpiece 801 is received by the photodetector array 805.

Figure 9A:
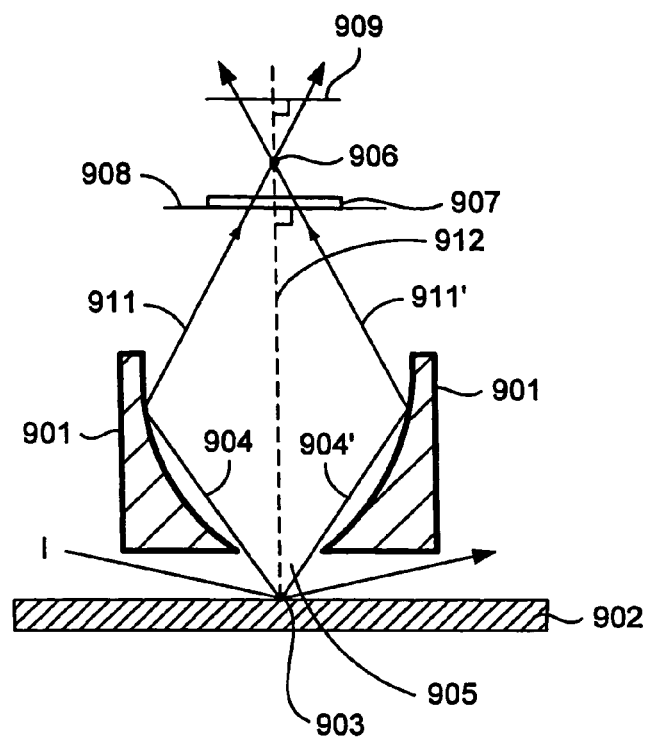
FIGS. 9(a)–9(c) are cross-sectional views of portions of darkfield inspection tools implementing reflector elements and suitable detection planes which can uniquely map the scattering angles of the scattered light beams to a photodetector array positioned in a detection plane in accordance with the principles of the present invention.

FIG. 9(a) depicts a cross-section view of an embodiment wherein the light shaping element comprises a reflector element 901. Many different types of reflector elements can be used. Examples include, but are not limited to, ellipsoid reflectors and parabolic reflectors. The depicted example is an ellipsoidal reflective surface. By way of additional description, an ellipsoid reflector is a three-dimensional reflective surface that can be described by the equation $$\frac{x^2}{a^2} + \frac{y^2}{b^2} + \frac{z^2}{c^2} = 1.$$

The reflector 901 is positioned such that the surface of the workpiece 902 lies at one of the foci 903 of the ellipsoid reflector 901. An incident light beam I impinges on the surface of the work piece at the foci 903. A portion of the light from the incident beam I is scattered. Some of this scattered light (schematically depicted by the scattered light beams 904, 904') enters a reflector 901 through an opening 905 in the bottom of the reflector 901. The reflective inner surface of the reflector reflects this scattered light 904, 904' out of the top of the reflector 901 as output beams (schematically, output beams 911, 911'). The output beams 911, 911' are directed toward the reflector's 901 second focal point 906. A photodetector array 907 is positioned at a detection plane 908. The detection plane 908 (and hence the associated photodetector array 907) are positioned such that the output beams 911, 911' are out of focus as they pass through the detection plane 908. Therefore, many different detection planes are suitable. All that is required is that the photodetector array 907 be positioned in a detection plane that is not at a focal point of the reflector 901. For example, the photodetector array 907 can be positioned above the focal point (e.g., in detection plane 909) or below the detection plane 908 (as shown). Factors in determining the exact position of the photodetector array include the size of the photodetector array, the amount of light capture desired, and the desired resolution. The scattered light beams 904, 904' are shaped (by the reflector 901) into a plurality of output light beams 911, 911' that have an output light distribution such that the position of each output light beam 911, 911', as it passes through a detection surface, is uniquely related to the scattering angles of the incoming scattered light beams 904, 904'. The photodetector array 907 receives this unfocussed light and produces electronic signals that can be used to quantify the surface of the workpiece 902. As shown in the depicted embodiment, the detection planes (908, 909 respectively) represent a small number of the many possible monitor planes and orientations. Each of the depicted detection planes 908, 909 is orthogonal to a line 912 extending between the first focal point 903 and the second focal point 906.

Figure 9B:
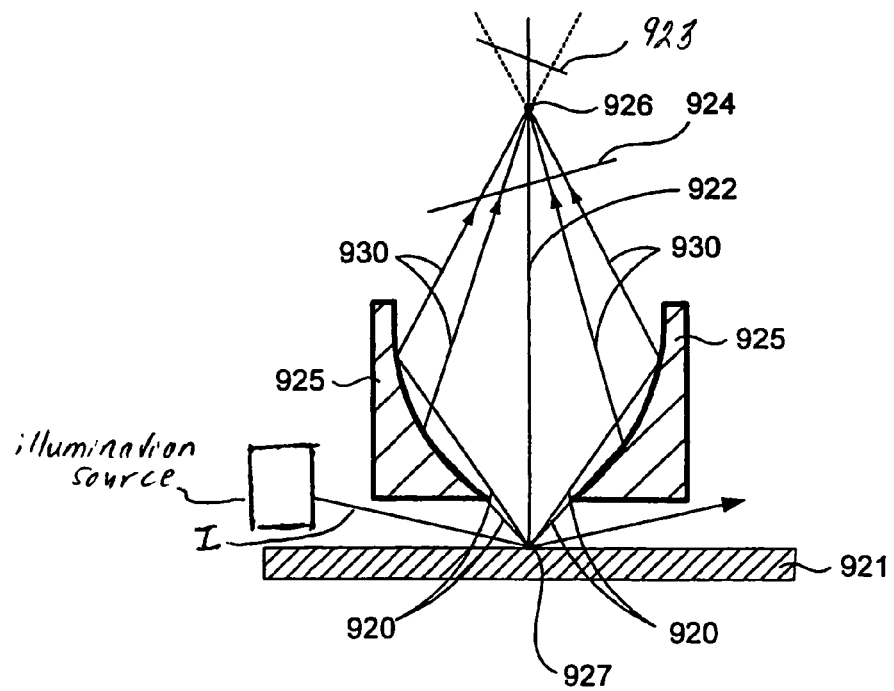

FIG. 9(b) illustrates alternative positioning of the detection planes. Again, an incident light beam I illuminates the surface of a workpiece 921. As described in FIG. 6(d), alternative monitor plane angles and orientations can be used. In FIG. 9(a), the monitor planes are all orthogonal to a line extending between the two foci of the ellipsoid reflector. However, this is not the only possible implementation. In the embodiment shown in FIG. 9(b), the monitor planes 923, 924 are positioned transverse to the line 922 extending between the two foci 926, 927 of the ellipsoid reflector 925 but not orthogonal to the line 922. A photodetector array positioned along one of the depicted monitor planes 923, 924 receives unfocussed light (schematically depicted by 930) from the reflector 925. This unfocussed light 930 has been shaped by the reflector 925 so that the scattered light beams 920 have an output light distribution such that the position of each output light beam as it passes through the detection plane (923, 924), is uniquely related to the scattering angles of the incoming scattered light beams 920. Such unfocussed light can then be detected and analyzed to evaluate the surface characteristics of the workpiece 921.

Figure 9C:
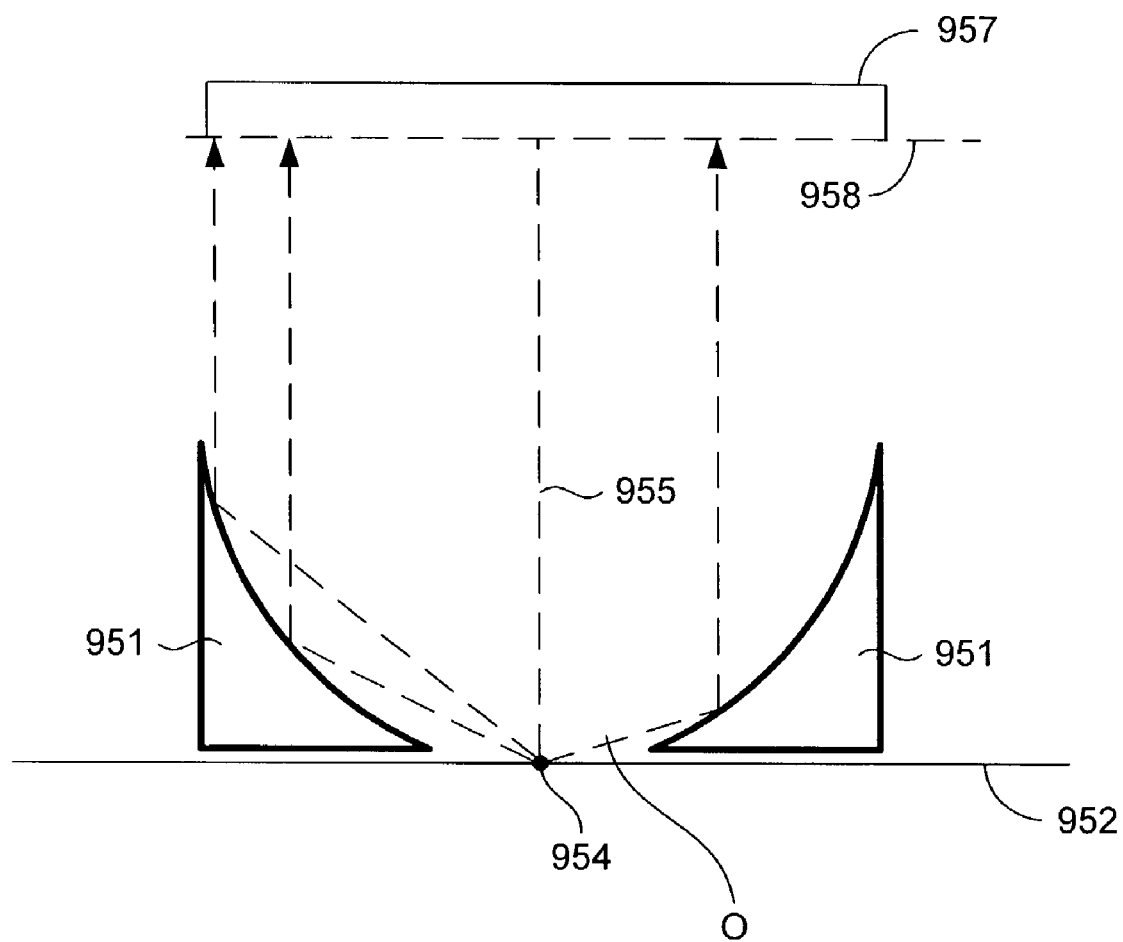

FIG. 9(c) depicts a cross-section view of another related embodiment wherein the reflector element comprises a paraboloid reflector 951. By way of additional description, a paraboloid reflector is a three-dimensional reflective surface that can be described, for example, by the equation $$\frac{x^2}{a^2} + \frac{y^2}{b^2} = z.$$

The reflector 951 is positioned such that the surface of the workpiece 952 lies at the foci 954 of the paraboloid reflector 951. As with the earlier depicted embodiments, an incident light beam impinges on the surface of the workpiece at the foci 954. A portion of the light from the incident beam is scattered. Some of this scattered light enters a reflector 951 through an opening O in the bottom of the reflector 951. The reflective inner surface of the reflector 951 reflects scattered light out of the top of the reflector 951 as a plurality of collimated output beams 953. A photodetector array 957 is positioned at a detection plane 958. The detection plane 958 (and hence the associated photodetector array 957) is positioned to intercept the output beams 953. Therefore, many different detection planes are suitable. As with the foregoing reflector embodiments, the output light distribution should be such that the position of each output light beam 953, as it impinges on the photodetector array 957, is uniquely related to the scattering angles of the incoming scattered light beams. The photodetector array 957 receives this light 953 and produces electronic signals that can be used to quantify the surface of the workpiece 952. As would be apparent to a person having ordinary skill in the art, many other suitable positions for the photodetector array 957 can be implemented in accordance with the principles of the present invention.

Figure 9D:
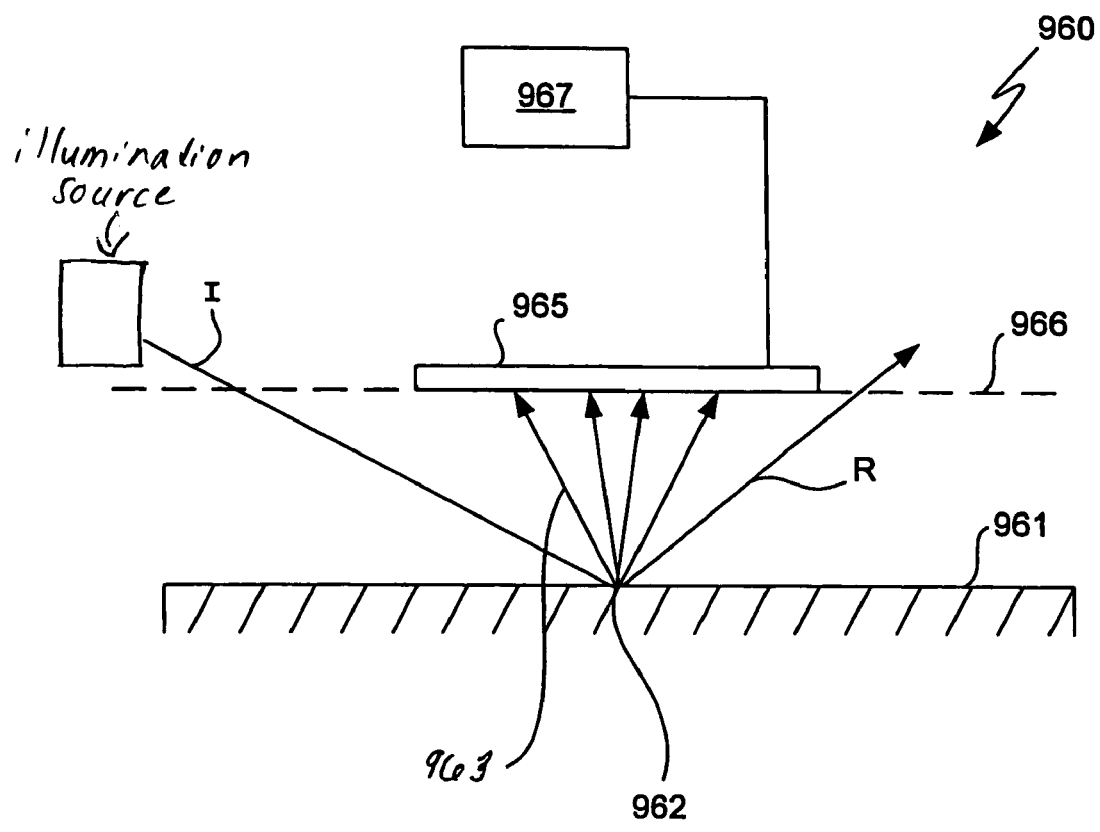
FIG. 9(d) is a cross-sectional view of portions of darkfield inspection tool implementing with no light-shaping element and one suitable detection plane, which uniquely maps the scattering angles of the scattered light beams to a photodetector array in accordance with the principles of the present invention.

In FIG. 9(d) the inventors depict a very basic embodiment 960 of the invention. An incident light beam I is directed onto an inspection point 962 of a workpiece 961. A plurality of scattered light beams 963 and a reflected beam R are also shown. A photodetector array 965 is positioned at a detection surface 966 to detect the scattered light beams 963. The photodetector array 965 produces electronic signals associated with the detected scattered light beams 963 which are received by the signal processing electronics 967 and then used to characterize defects on the workpiece 961. Notably absent from this embodiment is the light-shaping optics of previously described embodiments. Although such light-shaping optics can provide certain advantages, they are not required to practice the invention. All that is need is a photodetector array positioned at a detection surface where the position of the scattered light beams is uniquely related to the scattering angle of the scattered light beams. Thus, the photodetector array of the depicted embodiment can be positioned at virtually any detection surface and still accomplish the characterization of defects in the workpiece. It should be noted that the other embodiments depicted herein also commonly employ signal processing electronics to interpret and analyze the electronic signals produced by the photodetector arrays of the present invention. Additionally, the inventors specifically point out that detection planes can be replaced by detection surfaces. Also, the inventors contemplate that the photodetector arrays of the present invention can be curved rather than planar. Such arrays can be shaped into a variety of curved configurations including, but not limited to, cylindrical sections, parabolic sections, spherical sections, as well as other curved sections.

Figure 10:
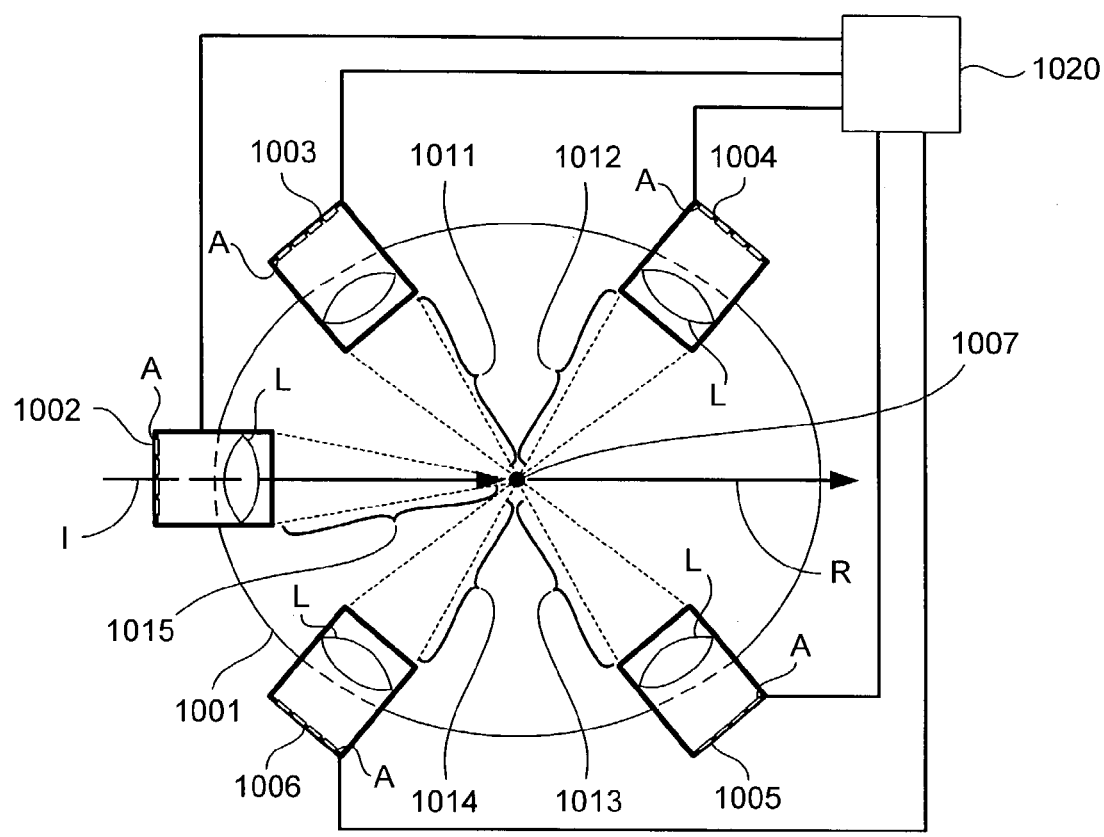
FIG. 10 is a plan view of a portion of darkfield inspection tool embodiment implementing a plurality of beam shaping elements to uniquely map the scattering angles of the scattered light beams to photodetector arrays in accordance with the principles of the present invention.

FIG. 10 is a schematic plan view of one possible embodiment constructed in accordance with the principles of the present invention. A workpiece 1001 is mounted in a darkfield scanning apparatus. A plurality of detector apparatus 1002, 1003, 1004, 1005, 1006 are mounted above the plane of the workpiece. Unlike conventional apparatus that use discrete detector elements, each of the plurality of detector apparatus 1002, 1003, 1004, 1005, 1006 incorporates a photodetector array A and, in some embodiments, beam-shaping optics L. Examples of such mountings have been previously discussed. An incident light beam I is directed onto an illumination spot 1007 on the surface of the workpiece 1001. As previously discussed, a portion of the incident light beam I is reflected as reflected beam R. Also, light is scattered from the surface. Portions of the scattered light 1011, 1012, 1013, 1014, 1015 are received by the detector apparatus (1002, 1003, 1004, 1005, 1006 respectively). The detector apparatus embodiments have been discussed extensively herein. Photodetector arrays of the detector apparatus 1002, 1003, 1004, 1005, 1006 detect the received scattered light 1011, 1012, 1013, 1014, 1015 at their respective locations. The photodetector arrays send two-dimensional light data to electronic signal processing circuitry 1020, which analyzes the data to determine the angle and intensity of the received scattered light 1011, 1012, 1013, 1014, 1015 to determine the location and type of defect on the surface of the workpiece 1001. Common electronic signal processing circuitry 1020 used in accordance with the principles of the invention can include digital signal processors (DSP), application specific integrated circuits (ASIC's), or other like electronic circuitry of the type commonly used by persons having ordinary skill in the art. Once a point on the surface is analyzed, another point is analyzed. The process continuing until either all desired points on the surface are analyzed or the entire surface is analyzed. This can be achieved by a number of methods (e.g., moving the workpiece or moving portions of the inspection tool). Common processes include rotating the workpiece so that the entire surface can be inspected in a spiral inspection pattern.

Figure 11A:
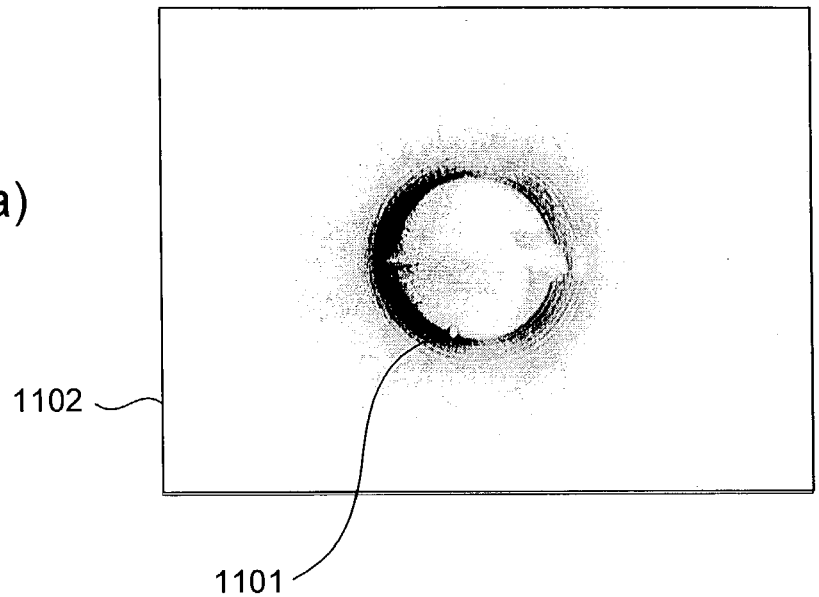
Figure 11B:
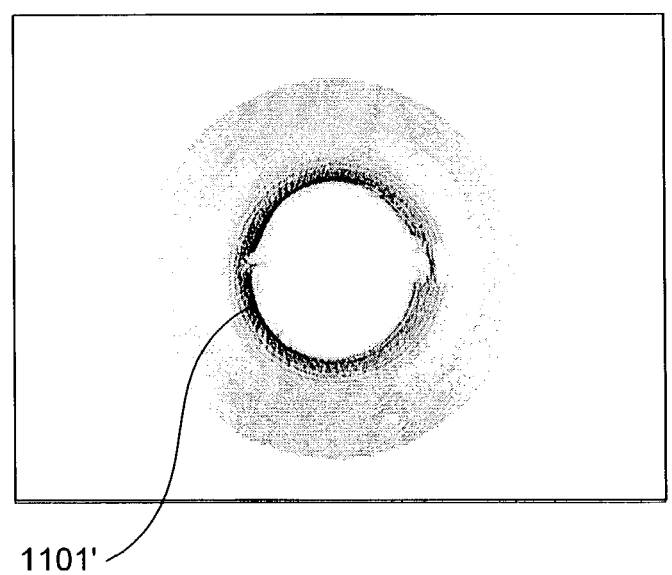

FIGS. 11(*a*)–11(*g*) depict some typical surface inspection results using an apparatus constructed in accordance with the principles of the present invention. Although many devices are contemplated for use in accordance with the principles of the present invention the depicted results are obtained using a modified SP 1 Surface Inspection System manufactured by KLA-Tencor Corporation of San Jose, Calif. In such a device the light-shaping element is an ellipsoidal reflector. Ordinarily, the SP 1 uses a pair of discrete detectors to detect scattered light in two angular ranges. In the modified device, the discrete detectors are removed and a photodetector array is positioned at an optical detector surface such that the resultant light distribution is uniquely related to scattering angles of the scattered light as the light distribution is incident on the photodetector array. In this particular embodiment, a conventional CCD camera, containing a photodetector array, is used to detect the light. It is important to note that the incident light beams of the embodiments of the invention can be directed onto the inspection surface at both normal and oblique angles. Also, the incident light can be filtered (e.g. to create light having different wavelengths, polarizations, etc.) as to alter the optical characteristics of the incident beams. In addition, the light scattered from the surface and received by the light-shaping element can be filtered (e.g. to create light having different polarizations or other optical characteristics) as to alter the optical characteristics of the shaped light beams before they are projected onto the photodetector array.

FIG. 11(*a*) shows an image detected by the photodetector array. The image reveals the presence of a polystyrene latex spherical particle 1101 resting on a portion of a silicon wafer surface 1102. The particle 1101 has been illuminated with incident light beam that is normal to the surface of the silicon wafer 1102. In FIG. 11(*b*) the same particle 1101' has been illuminated with an oblique (not at an angle normal to the surface) S-polarized incident light beam.

FIG. 11(*c*) shows yet another type of defect on an inspection surface. The image reveals the presence of a scratch 1103 in the inspection surface 1104. The scratch 1103 has been illuminated with incident light beam that is normal to the surface of the inspection surface 1104. Importantly, in this depiction the photodetector array is positioned in a fourier plane of the reflector. In contrast, as shown in FIG. 11(*d*), the same scratch 1103' has been illuminated with an oblique P-polarized incident light beam. As can easily be seen, the scratch 1103' generates a ring-shaped pattern.

FIG. 11(*e*) is a depiction of another type of defect on an inspection surface. The image depicts a crystalline stacking fault 1105 on an epitaxial silicon wafer surface 1106. The stacking fault 1105 has been illuminated with incident light beam that is normal to the surface of the wafer surface 1106. As can be seen in this depiction, the resulting pattern caused by the stacking fault 1105 is vaguely cruciform in shape. This is indicative of certain crystalline defects in the wafer surface. This is in contrast with, for example, the defect shown by FIG. 11(*f*). FIG. 11(*f*) shows a crystalline stacking fault with a "mound" formed thereon 1107. As with the stacking fault 1105 of FIG. 11(*e*), the stacking fault with a "mound" 1107 has been illuminated with incident light beam that is normal to the surface of the wafer surface. As can be seen in this depiction, the vaguely cruciform shape of FIG. 11(*e*) is significantly disrupted. This is indicative of a stacking fault with a "mound" on the wafer surface.

FIG. 11(*g*) depicts another type of defect on an inspection surface. The image depicts a pit with a mound 1108 on an epitaxial silicon wafer surface 1109. The pit with mound 1108 has been illuminated with incident light beam that is normal to the surface of the wafer surface 1109. As can be seen in this depiction, the resulting pattern caused by the pit with mound 1108 is a distorted annulus. Thus, it can easily seen from the foregoing Figs. that a variety of defects can be detected and quantified. Importantly, using the principles of the present invention, different types of defects can be readily distinguished from one another. This presents a significant advance over existing technologies.

Figure 12:
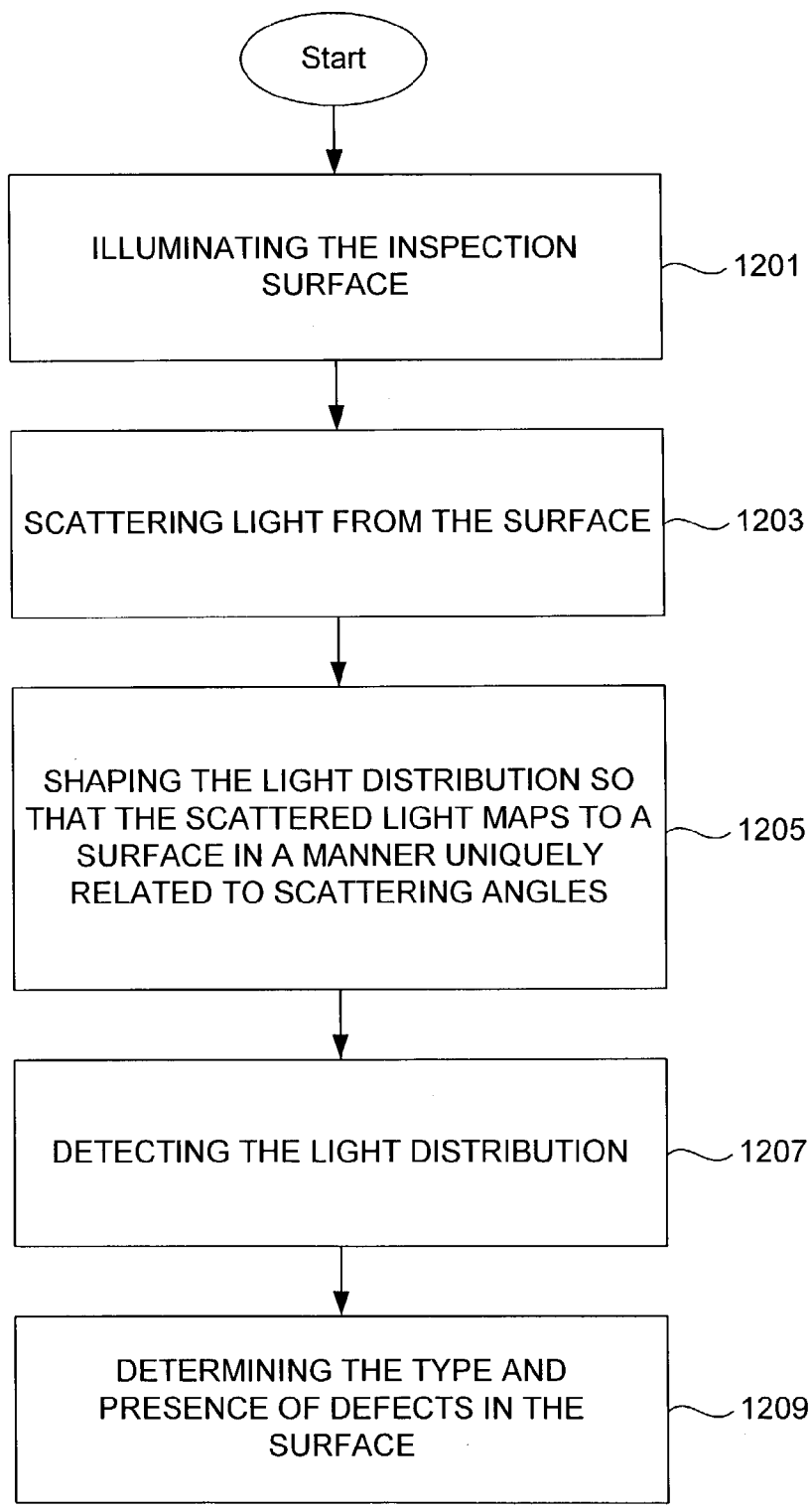
FIG. 12 is a flow diagram depicting a method embodiment in accordance with the principles of the present invention.

FIG. 12 is a flow diagram illustrating an embodiment of a process for inspecting a surface of a workpiece in accordance with the principles of the present invention. Such a surface inspection method comprises illuminating an inspection surface with light (Step 1201). Scattering a portion of the light from the surface (Step 1203). Upon which, the method includes shaping light scattered from the inspection surface into a light distribution such that the position of the light distribution as it passes through an optical detector surface is uniquely related to scattering angles of the light scattered from the inspection surface (Step 1205). Then, detecting the light distribution at the optical detector surface such that the scattering angles of the light scattered from the inspection surface can be determined from the position of the detected light distribution Step (1207). Determining whether defects are present on the inspection surface and determining the type of defect from said detected light (Step 1209).

The present invention has been particularly shown and described with respect to certain preferred embodiments and specific features thereof. However, it should be noted that the above-described embodiments are intended to describe the principles of the invention, not limit its scope. Therefore, as is readily apparent to those of ordinary skill in the art, various changes and modifications in form and detail may be made without departing from the spirit and scope of the invention as set forth in the appended claims. Other embodiments and variations to the depicted embodiments will be apparent to those skilled in the art and may be made without departing from the spirit and scope of the invention as defined in the following claims. In particular, it is contemplated by the inventors that photodetector arrays of the present invention are not limited to planar arrays. Photodetector arrays in accordance with the principles of the present invention can have a wide variety of shapes and can include photodetector arrays having curved surfaces. The inventors also contemplate a variety of reflector shapes (e.g., not limited to paraboloid and ellipsoid surfaces). Further, reference in the claims to an element in the singular is not intended to mean "one and only one" unless explicitly stated, but rather, "one or more". Furthermore, the embodiments illustratively disclosed herein can be practiced without any element, which is not specifically disclosed herein.

We claim:

1. A darkfield surface inspection tool comprising;
   an illumination source for directing a light beam onto a workpiece to generate scattered light;
   a reflective light-shaping element that collects the scattered light from an illuminated portion of the workpiece and shapes the scattered light into a resultant light distribution so that the position of the light beams of the resultant light distribution is uniquely related to scattering angles of the received scattered light as the resultant light distribution reaches a photosensitive detector array and wherein the light-shaping element comprises a reflective ellipsoid surface having a first foci and a second foci having an imaginary line that passes through the first foci and the second foci;
   wherein the illuminated surface of the workpiece is at the first foci; and
   wherein the detector array is positioned so that the array directly receives the resultant light distribution from the light-shaping element but does not intersect with the second foci.

2. A darkfield surface inspection tool as in claim 1 further including electronic circuitry for receiving data from the photosensitive detector array and determining an angular distribution of light intensity of the received scattered light based on data concerning at least one of the light intensity and the position of the resultant light distribution.

3. A darkfield surface inspection tool as in claim 1, wherein the reflective light-shaping element is configured to shape the light distribution into a Fourier distribution.

4. A darkfield surface inspection tool as in claim 1 further including electronic circuitry for receiving data from the photosensitive detector array and determining whether defects are present in the workpiece.

5. A darkfield surface inspection tool as in claim 4 wherein the electronic circuitry for receiving data from the photosensitive detector array is further capable of determining the type of said defects.

6. A darkfield surface inspection tool as in claim 1,
   wherein the photosensitive detector array has a curved configuration.

7. The darkfield surface inspection tool of claim 6, wherein the workpiece comprises a semiconductor wafer.

8. The darkfield surface inspection tool of claim 7, wherein the semiconductor wafer has a patterned surface comprising patterns of micro-circuitry elements.

9. The darkfield surface inspection tool of claim 6, wherein the workpiece comprises a mask reticle.

* * * * *

UNITED STATES PATENT AND TRADEMARK OFFICE
CERTIFICATE OF CORRECTION

| | | |
|---|---|---|
| PATENT NO. | : 7,061,598 B1 | Page 1 of 1 |
| APPLICATION NO. | : 10/315340 | |
| DATED | : June 13, 2006 | |
| INVENTOR(S) | : Bevis et al. | |

It is certified that error appears in the above-identified patent and that said Letters Patent is hereby corrected as shown below:

In the Specification:

Column 4, line 4, change "toot embodiment" to --tool embodiment--.

Signed and Sealed this

Twenty-sixth Day of December, 2006

JON W. DUDAS
*Director of the United States Patent and Trademark Office*